United States Patent
Fiss et al.

(10) Patent No.: US 10,683,540 B2
(45) Date of Patent: Jun. 16, 2020

(54) OLIGONUCLEOTIDE INHIBITOR OF DNA POLYMERASES

(71) Applicant: Roche Molecular Systems, Inc., Pleasanton, CA (US)

(72) Inventors: Ellen H. Fiss, Albany, CA (US); Joseph San Filippo, Dublin, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 10 days.

(21) Appl. No.: 16/012,402

(22) Filed: Jun. 19, 2018

(65) Prior Publication Data

US 2018/0291429 A1 Oct. 11, 2018

Related U.S. Application Data

(62) Division of application No. 14/562,351, filed on Dec. 5, 2014, now Pat. No. 10,036,061.

(60) Provisional application No. 61/919,520, filed on Dec. 20, 2013.

(51) Int. Cl.
| | |
|---|---|
| *C12Q 1/68* | (2018.01) |
| *C12N 15/113* | (2010.01) |
| *C12N 15/115* | (2010.01) |
| *C12N 9/99* | (2006.01) |
| *C12Q 1/686* | (2018.01) |

(52) U.S. Cl.
CPC ............. *C12Q 1/686* (2013.01); *C12N 9/99* (2013.01); *C12N 15/113* (2013.01); *C12N 15/115* (2013.01); *C12N 2310/16* (2013.01); *C12N 2310/531* (2013.01)

(58) Field of Classification Search
CPC .............. C12Q 1/686; C12Q 2521/531; C12Q 2527/101; C12N 2310/531
See application file for complete search history.

(56) References Cited

U.S. PATENT DOCUMENTS

| 8,026,068 B2 | 9/2011 | Pinsl-Ober et al. |
| 2007/0117114 A1 | 5/2007 | Rashtchian et al. |

FOREIGN PATENT DOCUMENTS

| EP | 2138590 A1 | 12/2009 |
| EP | 2202302 A1 | 6/2010 |
| JP | 2010004884 | 1/2010 |
| JP | 2010142229 | 7/2010 |
| WO | WO07/008728 | 1/2007 |
| WO | PCT/EP2014/078350 | 4/2015 |

OTHER PUBLICATIONS

Integrated DNA Technologies OligoAnalyzer 3.1 (2006), from web site https://www.idtdna.com/calc/analyzer, p. 1, results obtained for 29mer oligonucleotide. (Year: 2006).*
Dang, Chinh, et al. 1996, "Oligonucleotide Inhibitors of Taq DNA Polymerase Facilitate Detection of Low Copy Number Targets by PCR", J. Mol. Biol., 264:268-278.
Lasken RS et al., "Archaebacterial DNA polymerases tightly bind uracil-containing DNA", J Biol Chem., American Society for Biochemistry and Molecular Biology, US, Jul. 26, 1996;271(30):17692-17696.
Gill S et al., "Interaction of the Family-B DNA Polymerase from the Archaeon Pyrococcus furiosus with Deaminated Bases", J. Mol. Biol., Sep. 28, 2007; 372(4):855-863, Epub Jul. 21, 2007.
Richardson TT et al. "Novel inhibition of archael family-D DNA polymerase by uracil", Nucleic Acids Res., Apr. 2013; 41(7):4207-4218, Epub Feb. 13, 2013.
Lin Y et al. "Inhibition of multiple thermostable DNA polymerases by a heterodimeric aptamer", J. Mol. Biol. Aug. 3, 1997; 271(1):100-111.
Yakimovich, et al., "Influence of DNA Aptamer Structure on the Specificity of Binding to Taq DNA Polymerase," Biochemistry (Moscow) 68(2):228-235 (2003).
Office Action dated Jul. 14, 2017 for European Application No. 14828022.5, 5 pages.

* cited by examiner

*Primary Examiner* — David C Thomas
(74) *Attorney, Agent, or Firm* — David J. Chang (57) ABSTRACT

The invention comprises a reversible oligonucleotide inhibitor of nucleic acid polymerases. Methods of designing said inhibitors and using said inhibitors in amplification and detection of nucleic acid, particularly detection of RNA by RT-PCR are also disclosed.

11 Claims, 5 Drawing Sheets
Specification includes a Sequence Listing.

SEQUENCE LISTING

<160> NUMBER OF SEQ ID NOS: 6

<210> SEQ ID NO 1
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
cgatcatctc agaacattct tagcgttttg ttcttgtgta tgatcg                    46

<210> SEQ ID NO 2
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2
cgaucauctc agaacattct tagcgttttg ttcttgtgta ugaucg                    46

<210> SEQ ID NO 3
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 3
cgatcatctc agaacattct tagcgtttug uucuugtgta tgatcg                    46

<210> SEQ ID NO 4
<211> LENGTH: 46
<212> TYPE: DNA

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 4
cgaucauctc agaacattct tagcgtttug uucuugtgta ugaucg                     46

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gcgctagggc gctggcaagt gtagcggtca c                                     31

<210> SEQ ID NO 6
<211> LENGTH: 8
<212> TYPE: PRT
<213> ORGANISM: Unknown
<220> FEATURE:
<223> OTHER INFORMATION: Description of Unknown: Polymerase motif
      peptide

<400> SEQUENCE: 6

Asp Tyr Ser Gln Ile Glu Leu Arg
1               5
```

OLIGONUCLEOTIDE INHIBITOR OF DNA POLYMERASES

CROSS REFERENCE TO RELATED APPLICATION

This application is a divisional of U.S. patent application Ser. No. 14/562,351, filed on Dec. 5, 2014, the content of which is incorporated by reference herein in its entirety.

REFERENCE TO SEQUENCE LISTING

The instant application contains a Sequence Listing which has been submitted electronically in ASCII format and is hereby incorporated by reference in its entirety. Said ASCII copy, created on Oct. 31, 2014, is named 31881_US1_SL.txt and is 1,912 bytes in size.

FIELD OF THE INVENTION

The invention relates to the field of nucleic acids amplification and specifically, to reducing non-specific amplification by a thermostable DNA polymerase via the use of a reversible oligonucleotide inhibitor of the polymerase.

BACKGROUND OF THE INVENTION

The Polymerase Chain Reaction (PCR) and real-time PCR have been widely accepted in the research and clinical fields as rapid and specific methods of detecting a target nucleic acid. However, the problem of non-specific amplification, i.e., amplification of non-target sequences, is often a limiting factor in achieving high sensitivity and specificity required for clinical applications. See Mackay, I. M. (2004) *Real-time PCR in the microbiology laboratory*, Clin. Microbiol. Infect. 10:190.

The non-specific amplification is thought to result from extension of primers annealed to secondary, partially complementary sites in the genome or to primer cross-annealing or self-annealing. The presence of non-specific extension products has been attributed to polymerase activity at ambient temperature where such partially complementary primer-template duplexes are stable. (Chou et al. (1992) *Prevention of pre-PCR mis-priming and primer dimerization improves low-copy-number amplifications* Nucleic Acid Res. 20:1717). Accordingly, methods of inhibiting the primer extension activity of the polymerase at ambient temperature have been devised. These methods termed "hot start" assure that the polymerase becomes fully active only when the temperature is high enough to destabilize non-specific primer-template complexes so that extension of the primers at non-specific sites is avoided.

One hot start method involves an oligonucleotide that binds and inhibits the polymerase at low temperature, but not at high temperature. See Dang and Jayasena (1996) *Oligonucleotide inhibitors of Taq DNA polymerase facilitate detection of low copy number targets by PCR* J. Mol. Biol. 264:268. These oligonucleotides are extremely specific for and have high affinity to the target enzyme.

The hot-start approach however is not suitable for reverse transcription PCR (RT-PCR) applications where the reverse transcriptase requires temperatures below 50° C. Certain thermostable DNA polymerases have reverse transcription activity, allowing the use of a single enzyme to perform reverse transcription and amplification of cDNA (RT-PCR) in the same reaction mixture. See Myers and Gelfand (1991) *Reverse transcription and DNA amplification by a Thermus thermophilus DNA polymerase*, Biochemistry 30:7661. However, RNA is labile at high temperature in the presence of divalent ions necessary for polymerase activity. For that reason, reverse transcription is carried out at lower temperature (50-60° C.) prior to commencement of the traditional PCR thermocycling. A typical oligonucleotide aptamer has melting temperature close to 60° C. and does not sufficiently release the inhibition of the polymerase at lower temperatures. It is therefore desirable to obtain a reversible polymerase inhibitor that could release inhibition at lower temperatures.

SUMMARY OF THE INVENTION

In one embodiment, the invention is a reversible inhibitor of nucleic acid polymerases comprising a single-stranded DNA oligonucleotide having one or more regions of double-stranded secondary structure, wherein at least one of said regions comprises at least one uracil base. The double-stranded secondary structure may be stable under ambient temperature in a PCR mixture. In some embodiments, the reversible inhibitor has SEQ ID NO:1 wherein one or more thymine bases are replaced with a uracil base, e.g., SEQ ID NOs: 2-4.

In another embodiment, the invention is a method of designing a reversible inhibitor of nucleic acid polymerases comprising designing a single-stranded DNA oligonucleotide having one or more regions of double-stranded secondary structure, wherein at least one of said regions comprises at least one uracil base. The oligonucleotide may be selected from a mixture of oligonucleotides using systematic evolution of ligands by exponential enrichment (SELEX).

In yet another embodiment, the invention is a method of reversibly inhibiting a nucleic acid polymerase in a reaction mixture comprising contacting the mixture with a single-stranded DNA oligonucleotide having one or more regions of double-stranded secondary structure, wherein at least one of said regions comprises at least one uracil base. The method may further comprise contacting the mixture with a uracil-N-glycosylase, optionally in the temperature range of 40-65° C. The method may further comprise contacting the sample with a polyamine, for example, a polyamine is selected from spermidine, spermine and trimethylenediamine.

In yet another embodiment, the invention is a method of amplifying a target nucleic acid comprising prior to amplification, contacting a reaction mixture containing the target nucleic acid with a single-stranded DNA oligonucleotide having one or more regions of double-stranded secondary structure, wherein at least one of said regions comprises at least one uracil base. The method may further comprise prior to amplification, contacting the sample with a uracil-N-glycosylase and optionally, with a polyamine, such as for example, spermidine, spermine or trimethylenediamine.

In yet another embodiment, the invention is a kit for amplifying a target nucleic acid containing a reversible inhibitor of a nucleic acid polymerase comprising a single-stranded DNA oligonucleotide having one or more regions of double-stranded secondary structure, wherein at least one of said regions comprises at least one uracil base. The kit may further comprise uracil-N-glycosylase and optionally, a polyamine, such as for example, spermidine, spermine or trimethylenediamine.

In yet another embodiment, the invention is a reaction mixture for amplifying a target nucleic acid containing a reversible inhibitor of a nucleic acid polymerase comprising a single-stranded DNA oligonucleotide having one or more regions of double-stranded secondary structure, wherein at least one of said regions comprises at least one uracil base. The reaction mixture may further comprise uracil-N-glycosylase and optionally, a polyamine, such as for example, spermidine, spermine or trimethylenediamine.

DETAILED DESCRIPTION OF THE INVENTION

Definitions

The terms "nucleic acid," and "oligonucleotide" refer to target sequences and probes. The terms are not limited by length and are generic to linear polymers of deoxyribonucleotides (single-stranded or double-stranded DNA), ribonucleotides (RNA), and any other N-glycoside of a purine or pyrimidine base, including adenosine, guanosine, cytidine, thymidine and uridine and modifications of these bases.

The term "conventional" or "natural" when referring to nucleic acid bases, nucleoside triphosphates, or nucleotides refers to those which occur naturally in the polynucleotide being described (i.e., for DNA these are adenine or dATP, guanine or dGTP, cytosine or dCTP and thymine or dTTP and for RNA, these are adenine or ATP, guanine or GTP, cytosine or CTP and uracil or UTP).

The term "unconventional," "non-natural," or "modified" when referring to a nucleic acid base, nucleoside, or nucleotide includes nucleic acid base, nucleoside, or nucleotide that does not occur in nucleic acids found in nature but is a modification, derivation, or analogue of conventional bases, nucleosides, or nucleotides. For example, dITP, and 7-deaza-dGTP do not occur in nucleic acids in nature but are frequently utilized in place of dGTP and 7-deaza-dATP can be utilized in place of dATP in in vitro DNA synthesis reactions, such as sequencing. Certain unconventional nucleotides are modified at the 2' position of the ribose sugar in comparison to conventional dNTPs. Ribonucleotides are unconventional nucleotides as substrates for DNA polymerases. As used herein, unconventional nucleotides include, but are not limited to, compounds used as terminators for nucleic acid sequencing. Exemplary terminator compounds include but are not limited to those compounds that have a 2',3' dideoxy structure and are referred to as dideoxynucleoside triphosphates, e.g, ddATP, ddTTP, ddCTP and ddGTP. Additional examples of terminator compounds include 2'-PO$_4$ analogs of ribonucleotides (see, e.g., U.S. Pat. No. 7,947,817). Other unconventional nucleotides include phosphorothioate dNTPs ([[α]-S]dNTPs), 5'-[α]-borano-dNTPs, [α]-methyl-phosphonate dNTPs, and ribonucleoside triphosphates (rNTPs). Unconventional bases may be labeled with radioactive isotopes such as $^{32}$P, $^{33}$P, or $^{35}$S; fluorescent labels; chemiluminescent labels; bioluminescent labels; hapten labels such as biotin; or enzyme labels such as streptavidin or avidin. Fluorescent labels may include dyes that are negatively charged, such as dyes of the fluorescein family, or dyes that are neutral in charge, such as dyes of the rhodamine family, or dyes that are positively charged, such as dyes of the cyanine family. Dyes of the fluorescein family include, e.g., FAM, HEX, TET, JOE, NAN and ZOE. Dyes of the rhodamine family include Texas Red, ROX, R110, R6G, and TAMRA. Various dyes or nucleotides labeled with FAM, HEX, TET, JOE, NAN, ZOE, ROX, R110, R6G, Texas Red and TAMRA are marketed by Perkin-Elmer (Boston, Mass.), Applied Biosystems (Foster City, Calif.), or Invitrogen/Molecular Probes (Eugene, Oreg.). Dyes of the cyanine family include Cy2, Cy3, Cy5, and Cy7 and are marketed by GE Healthcare Biosciences (Pittsburgh, Pa.).

The term "oligonucleotide" refers to a nucleic acid polymer that includes at least two nucleic acid monomer units (e.g., nucleotides). An oligonucleotide typically includes from about six to about 175 nucleotides, more typically from about eight to about 75 nucleotides, e.g., about 15, about 20, about 25, about 30, about 35, or more nucleotides). The exact size of an oligonucleotide will depend on many factors, including the ultimate function or use of the oligonucleotide. Many methods exist for preparation of oligonucleotides, e.g., isolation of an existing or natural sequence, DNA replication or amplification, reverse transcription, cloning and restriction digestion of appropriate sequences, or direct chemical synthesis by a method such as the phosphotriester method of Narang et al. (*Meth. Enzymol.* 68:90-99, 1979); the phosphodiester method of Brown et al. (*Meth. Enzymol.* 68:109-151, 1979); the diethylphosphoramidite method of Beaucage et al. (*Tetrahedron Lett.* 22:1859-1862, 1981); the triester method of Matteucci et al. (*J. Am. Chem. Soc.* 103:3185-3191, 1981).

The term "probe" refers to an oligonucleotide that selectively hybridizes to a target nucleic acid under suitable conditions.

The terms "target sequence" or "target" refer to a region of a nucleic acid sequence that is to be analyzed.

The term "sample" refers to any composition containing or presumed to contain nucleic acid. This includes a sample of tissue or fluid isolated from an individual for example, skin, plasma, serum, spinal fluid, lymph fluid, synovial fluid, urine, tears, blood cells, organs, bone marrow and tumors, including the fresh or fresh-frozen tissue and formalin-fixed paraffin embedded tissue (FFPET), and also to samples of in vitro cultures established from cells taken from an individual, and nucleic acids isolated therefrom.

The term "aptamer" refers to an oligonucleotide that specifically recognizes and binds to DNA polymerase, and efficiently inhibits the polymerase activity as described in U.S. Pat. No. 5,693,502.

The term "mutant," in the context of DNA polymerases of the present invention, means a polypeptide, typically recombinant, that comprises one or more amino acid substitutions relative to a corresponding, naturally-occurring or unmodified DNA polymerase.

The term "thermostable polymerase," refers to an enzyme that is stable at elevated temperatures, is heat resistant, and retains sufficient activity to effect subsequent polynucleotide extension reactions and does not become irreversibly denatured (inactivated) when subjected to the elevated temperatures for the time necessary to effect denaturation of double-stranded nucleic acids. Thermostable DNA polymerases from thermophilic bacteria include, e.g., DNA polymerases from *Thermotoga maritima, Thermus aquaticus, Thermus thermophilus, Thermus flavus, Thermus filiformis, Thermus* species Sps17, *Thermus* species Z05, *Thermus caldophilus, Bacillus caldotenax, Thermotoga neopolitana*, and *Thermosipho africanus*.

The term "thermoactive" refers to an enzyme that maintains its catalytic properties at temperatures commonly used for annealing and extension steps in PCR reactions (i.e., 45-80° C.). Thermoactive enzymes may or may not be thermostable. Thermoactive DNA polymerases can be DNA or RNA dependent from thermophilic species or from mesophilic species including, but not limited to, *Escherichia coli, Moloney murine* leukemia viruses, and *Avian myoblastosis* virus.

In the context of DNA polymerases, "correspondence" to another sequence (e.g., regions, fragments, nucleotides or amino acid positions in the sequence) is based on the convention of numbering according to nucleotide or amino acid position and then aligning the sequences in a manner that maximizes the percentage of sequence identity. Because not all positions within a given "corresponding region" need be identical, non-matching positions within a corresponding region may be regarded as "corresponding positions." Accordingly, as used herein, referral to an "amino acid position corresponding to amino acid position [X]" of a specified DNA polymerase refers to equivalent positions, based on alignment, in other DNA polymerases and polymerase families.

The terms "identical" or "identity," or percent identity in the context of two or more nucleic acids or polypeptide sequences, refer to two or more sequences or subsequences that are the same. Sequences are "substantially identical" to each other if they have a specified percentage of nucleotides or amino acid residues that are the same (e.g., at least 60%, at least 65%, at least 70%, at least 75%, at least 80%, at least 85%, at least 90%, or at least 95% identity over a specified region), when compared and aligned for maximum correspondence over a comparison window, or designated region as measured using one of the following sequence comparison algorithms or by manual alignment and visual inspection. These definitions also refer to the complement of a test sequence.

The terms "similarity" or "percent similarity," in the context of two or more polypeptide sequences, refer to two or more sequences or subsequences that have a specified percentage of amino acid residues that are either the same or similar as defined by a conservative amino acid substitutions (e.g., 60% similarity, optionally 65%, 70%, 75%, 80%, 85%, 90%, or 95% similar over a specified region), when compared and aligned for maximum correspondence over a comparison window, or designated region as measured using one of the following sequence comparison algorithms or by manual alignment and visual inspection. Sequences are "substantially similar" to each other if they are at least 20%, at least 25%, at least 30%, at least 35%, at least 40%, at least 45%, at least 50%, or at least 55% similar to each other.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, for example, by the local homology algorithm of Smith and Waterman (*Adv. Appl. Math.* 2:482, 1970), by the homology alignment algorithm of Needleman and Wunsch (*J. Mol. Biol.* 48:443, 1970), by the search for similarity method of Pearson and Lipman (*Proc. Natl. Acad. Sci. USA* 85:2444, 1988), or by computerized implementations of these algorithms e.g., BLAST, BLASTN, GAP, BESTFIT, FASTA, and TFASTA, or by manual alignment and visual inspection (see, e.g., Ausubel et al., *Current Protocols in Molecular Biology* (1995 supplement)).

The terms "$C_p$ value" or "crossing point" value, or "$C_t$ value" or "threshold cycle" value are used interchangeably to refers to a value that allows quantification of input target nucleic acids. The $C_t$ value can be determined e.g., according to the second-derivative maximum method, see Van Luu-The, et al., (2005) *Improved real-time RT-PCR method for high-throughput measurements using second derivative calculation and double correction*, BioTechniques, 38:287.

The term "PCR efficiency" refers to an indication of cycle to cycle amplification efficiency for the perfectly matched primer template. PCR efficiency is calculated for each condition using the equation: % PCR efficiency=$(10^{(-slope)}-1) \times 100$, wherein the slope was calculated by linear regression with the log copy number plotted on the y-axis and $C_t$ plotted on the x-axis.

The present invention comprises a reversible inhibitor of DNA polymerases having the form of an oligonucleotide. Specifically, the oligonucleotide is a DNA oligonucleotide (i.e., composed of deoxyribonucleotides) including one or more deoxyuridine (dU) nucleotides (dU-containing inhibitor oligonucleotide). The sequence of the oligonucleotide enables the formation of a secondary structure comprising one or more regions of double stranded secondary structure. The oligonucleotide forms a stable secondary structure under ambient temperature conditions in the typical reaction mixture, e.g., a PCR mixture. According to the invention, the one or more uracils are positioned within the regions of the double stranded secondary structure. The inhibitory properties of the oligonucleotide of the present invention are not dependent on the exact nucleotide sequence, but rather on the conformation or shape of the secondary structure formed by the sequence and the melting temperature ($T_m$) of that structure. At a temperature below the $T_m$ e.g., at ambient temperature in a typical reaction mixture, the shape assumed by the oligonucleotide allows it to form the oligonucleotide-enzyme complex. The oligonucleotide reversibly inhibits the polymerase enzyme while associated with the enzyme in an oligonucleotide-enzyme complex.

It has been shown that introducing non-natural nucleotide can affect the formation and $T_m$ (and hence stability) of the secondary structure formed by the oligonucleotide and thus its inhibitory properties. To that end, the DNA oligonucleotides have been modified to contain ribonucleotides, nucleotide analogs, nucleotides with unconventional bases, non-nucleotide linkers or combinations thereof. (See e.g., U.S. Pat. No. 6,183,679 for description of such non-natural nucleotides in inhibitor oligonucleotides). One of skill in the art can design an inhibitor oligonucleotide (including a dU-containing inhibitor oligonucleotide of the present invention) with a melting temperature and shape suitable for a particular enzyme.

In some embodiments, the dU-containing inhibitor oligonucleotide is designed by replacing one or more thymines with uracils in the existing aptamer NTQ21-46A (also referred to as U0) (SEQ ID NO: 1) 5'-CGATCATCTCAGAACATTCTTAGCGTTTTGTTCTTGTGTATGATCG-3'. In variations of this embodiment, the dU-containing inhibitor oligonucleotide is one of the following sequences:

U1

(SEQ ID NO: 2)
5'-CGAUCAUCTCAGAACATTCTTAGCGTTTTGTTCTTGTGTAUGAUCG-3'

-continued

U2

(SEQ ID NO: 3)

5'-CGATCATCTCAGAACATTCTTAGCGTTTUGUUCUUGTGTATGATCG-3'

U3

(SEQ ID NO: 4)

5'-CGAUCAUCTCAGAACATTCTTAGCGTTTUGUUCUUGTGTAUGAUCG-3'.

Figure 1:
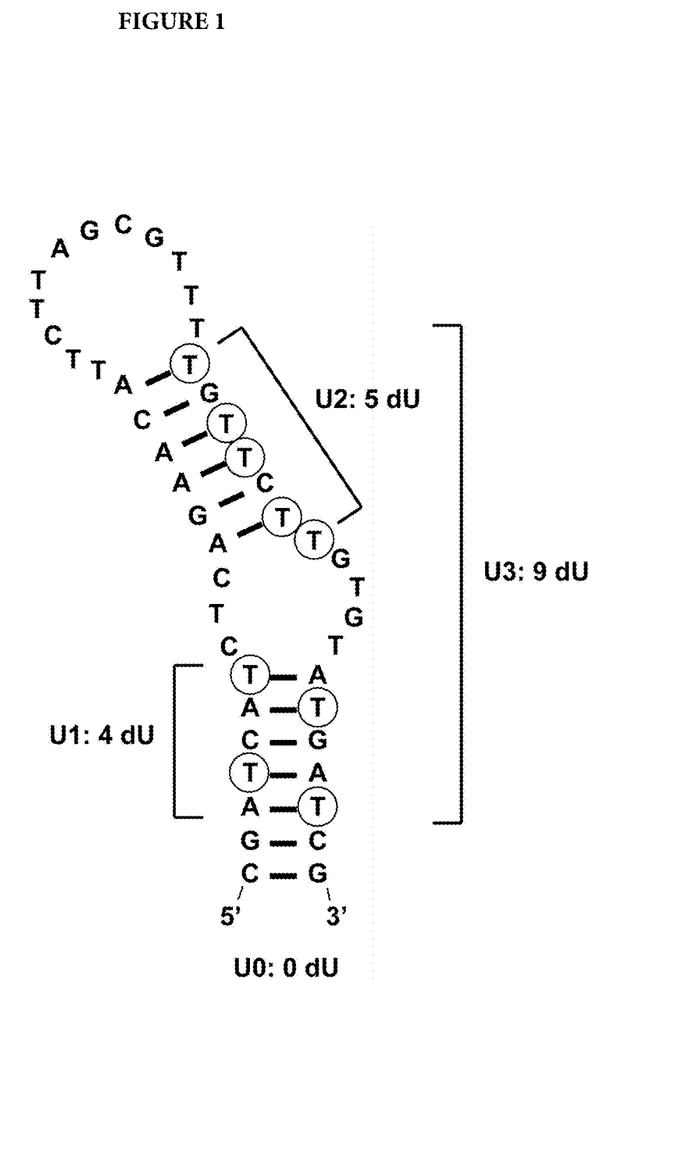
FIG. 1 shows the predicted secondary structure of the oligonucleotide SEQ ID NO: 1 and positions where Ts were replaced with Us to form SEQ ID NOs: 2-4.
Figure 2:
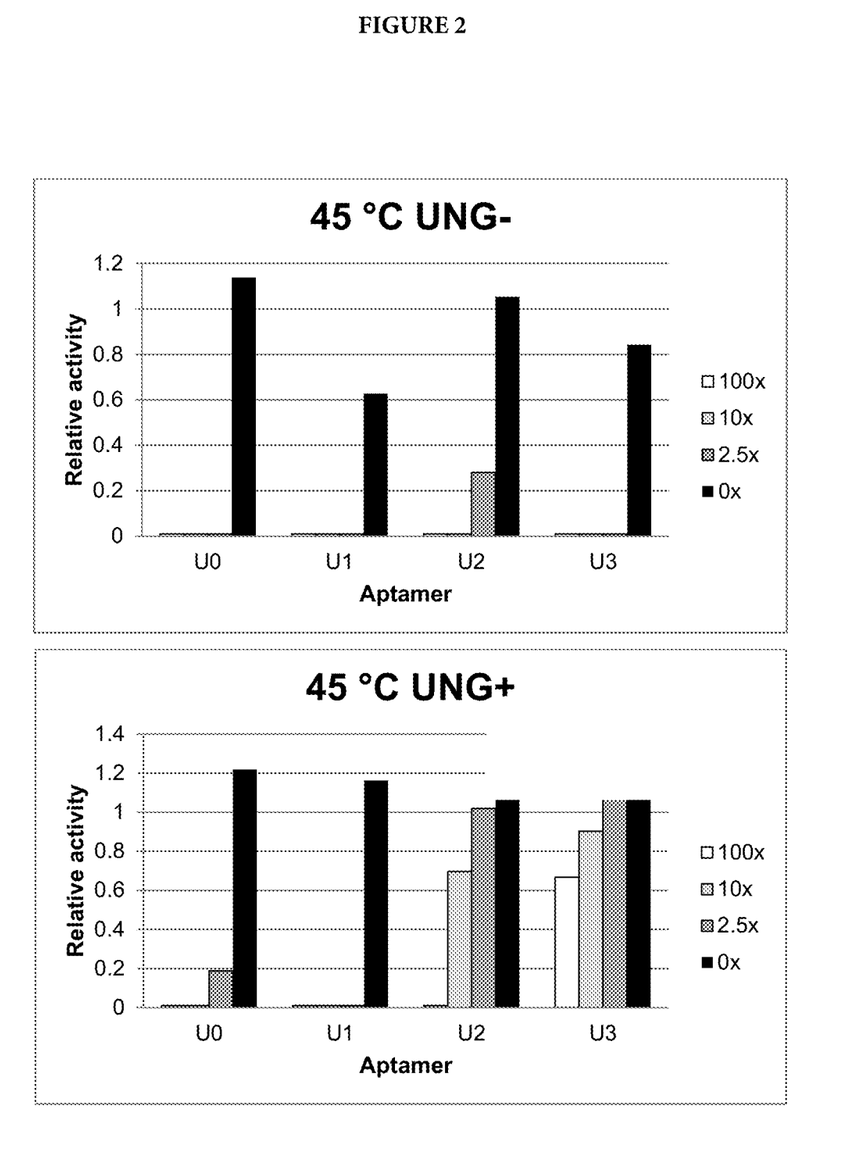
FIGS. 2-5 show results of primer extension in the presence of SEQ ID NOs: 1-4 at various temperatures.
Figure 3:
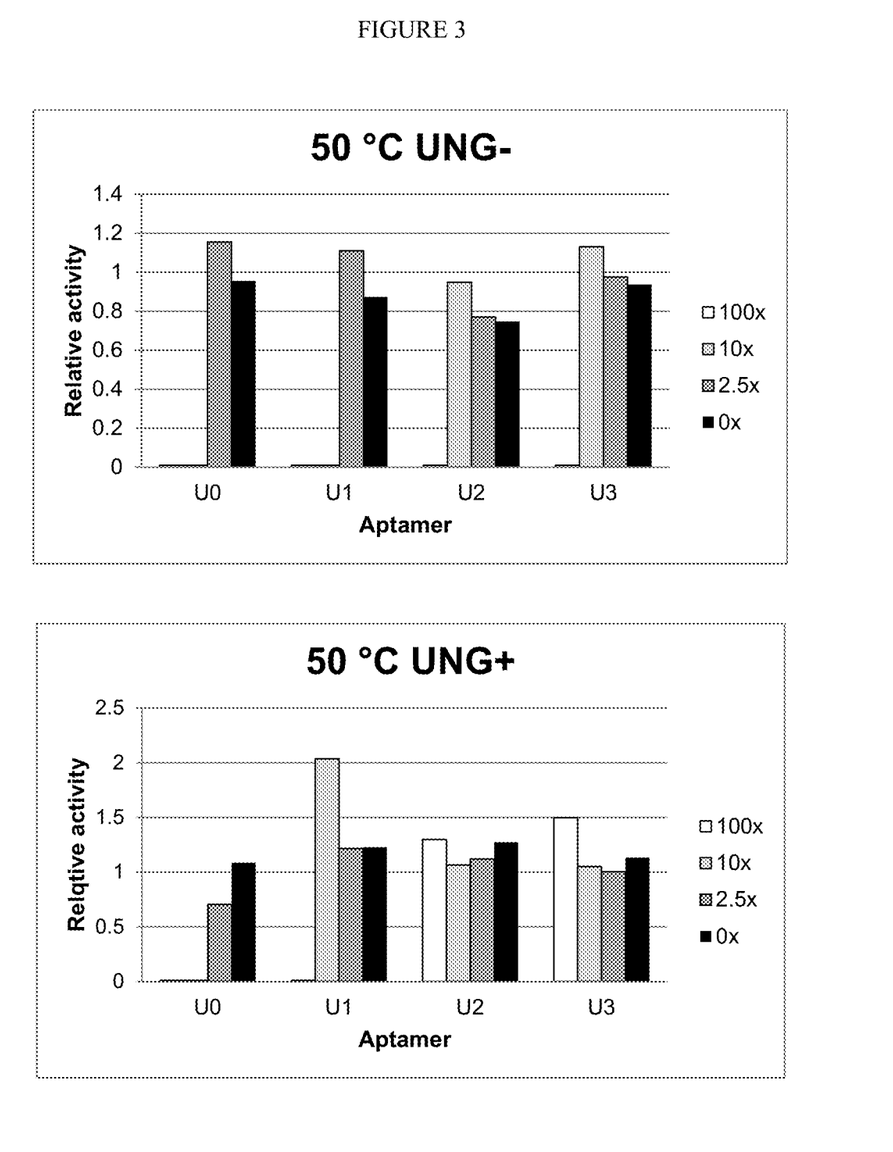
Figure 4:
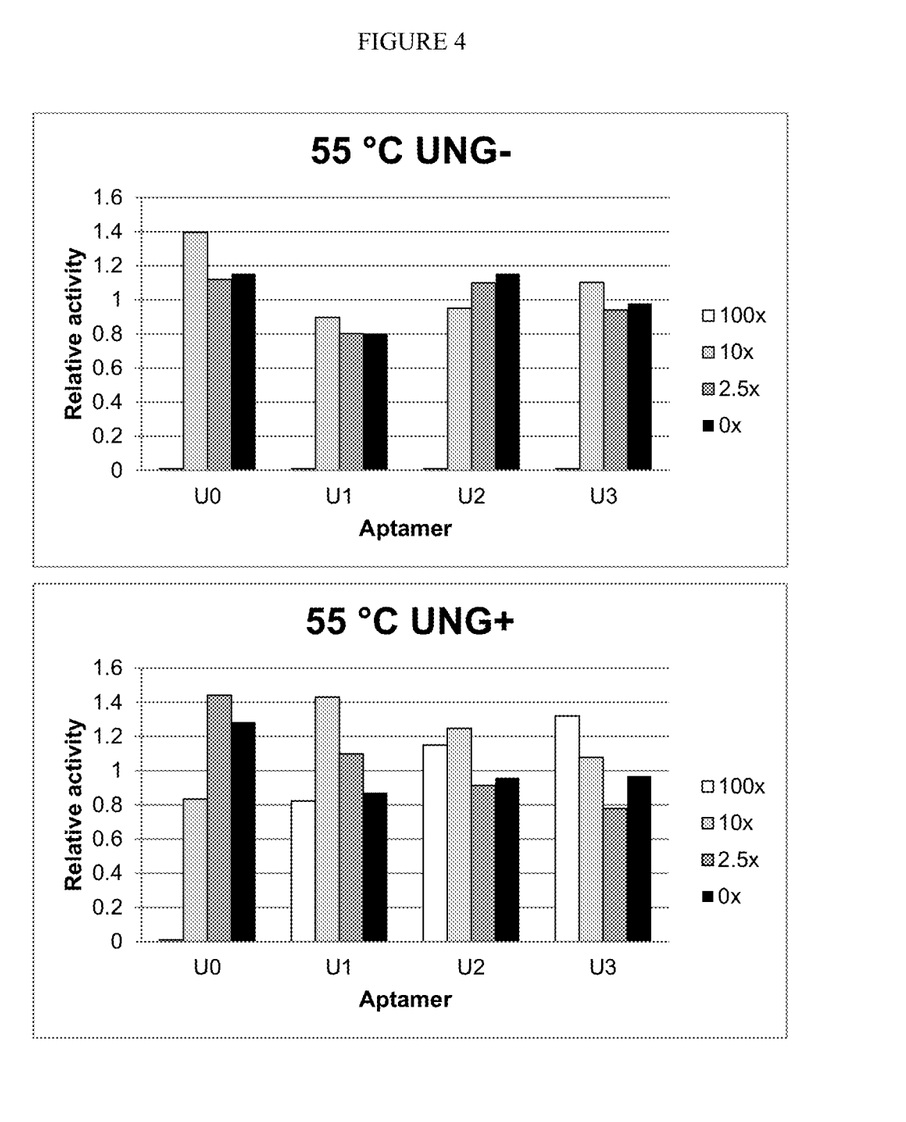
Figure 5:
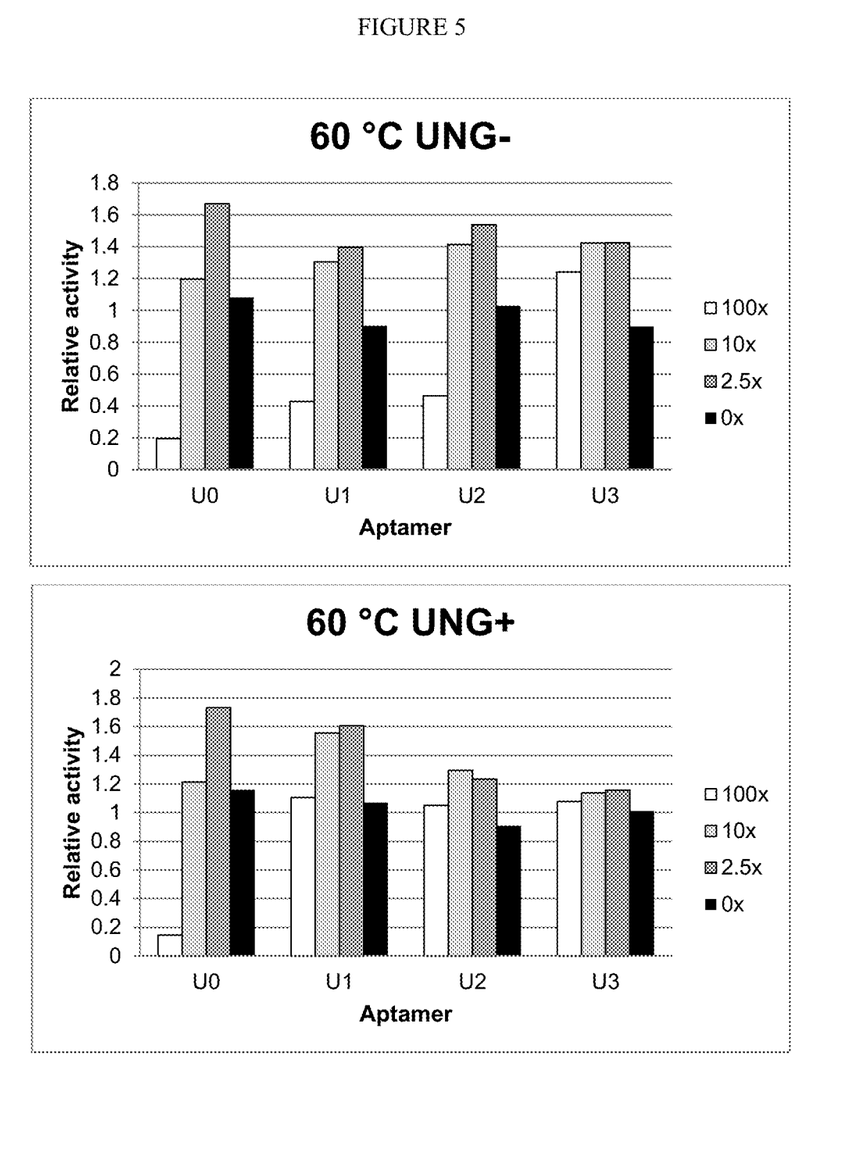

Predicted secondary structure of the aptamer NTQ21-46A (U0) and U1, U2 and U3 is shown in FIG. 1.

One of skill in the art can easily design similar dU-containing inhibitor oligonucleotides by replacing thymines with uracils or by introducing uracils in any other positions within the oligonucleotide, e.g., in SEQ ID NO: 1 or in a sequence of another known or novel inhibitor oligonucleotide.

The examples below describe application of the method of the present invention to reversibly inhibiting a DNA polymerase from the *Thermus* species Z05 (disclosed in International Application Pub. No. WO1992/06200). However, the method is equally applicable to other DNA polymerases. Analysis of X-ray crystal structures has revealed that DNA polymerases from various organisms fold into similar three dimensional structures. The overall folding pattern of DNA polymerases resembles the human right hand and contains three distinct subdomains termed "palm," "fingers," and "thumb." (See Beese et al., (1993) *Structure of DNA polymerase I Klenow fragment bound to duplex DNA* Science 260:352; Patel et al., (1995) *Insights into DNA polymerization mechanisms from structure and function analysis of HIV-1 reverse transcriptase* Biochemistry 34:5351). While the structure of the fingers and thumb subdomains vary greatly between polymerases that differ in size and in cellular functions, the catalytic palm subdomains are all superimposable. For example, motif A, which interacts with the incoming dNTP and stabilizes the transition state during chemical catalysis, is superimposable with a mean deviation of about one Å amongst mammalian pol α and prokaryotic pol I family DNA polymerases (Wang et al., (1997) *Crystal structure of a pol alpha family replication DNA polymerase from bacteriophage RB69* Cell 89:1087. The primary amino acid sequence of DNA polymerase active sites is exceptionally conserved. In the case of motif A, for example, the sequence DYSQIELR (SEQ ID NO: 6) is retained in polymerases from organisms separated by many millions years of evolution, including, e.g., *Thermus aquaticus, Chlamydia trachomatis* and *Escherichia coli*.

In some embodiments, the U-containing inhibitor oligonucleotide according to the present invention can be designed and oligonucleotide sequences disclosed here can be used and further optimized to similarly reversibly inhibit other thermostable or thermoactive DNA polymerases, e.g. DNA polymerases from *Thermotoga maritima, Thermus aquaticus, Thermus thermophilus, Thermus flavus, Thermus filiformis, Thermus* species Sps17, *Thermus caldophilus, Bacillus caldotenax, Thermotoga neopolitana*, and *Thermosipho africanus* or similar DNA polymerases at least 95% identical thereto.

More generally, the U-containing inhibitor oligonucleotide according to the present invention can be designed to similarly reversibly inhibit other thermostable or thermoactive enzymes such as ligases, helicases and nucleases (including nuclease activities of DNA polymerases). Reversible oligonucleotide inhibitors for such enzymes have been described, see, e.g., U.S. Pat. No. 8,470,531. These oligonucleotide inhibitors can be changed into the U-containing oligonucleotide inhibitors of the present invention to benefits from the improved properties described herein.

In some embodiments, the invention is a method of designing a reversible inhibitor of nucleic acid polymerases comprising designing a single-stranded DNA oligonucleotide having one or more regions of double-stranded secondary structure, wherein at least one of said regions comprises at least one uracil base.

The U-containing inhibitor oligonucleotide of the present invention can be designed and optimized using an in vitro selection procedure systematic evolution of ligands by exponential enrichment (SELEX) described in the U.S. Pat. No. 6,183,679. Briefly, in the SELEX method, a mixture of oligonucleotides with different sequences is contacted with the target, e.g., an enzyme. The mixture of oligonucleotides that bind the target are partitioned, amplified and subjected to another round of selection until a small number of oligonucleotides with maximum affinity to the target are identified.

The U-containing inhibitor oligonucleotide of the present invention can be prepared by any suitable method, for example by direct chemical synthesis by the phosphotriester method of Narang et al. (1979) *Meth. Enzymol.* 68:90-99; the phosphodiester method of Brown et al. (1979) *Meth. Enzymol.* 68:109-151; the diethylphosphoramidite method of Beaucage et al. (1981) *Tetrahedron Lett.* 22:1859-1862; the triester method of Matteucci et al., (1981) *J. Am. Chem. Soc.* 103:3185-3191; any one of the automated synthesis methods; or the solid support method of U.S. Pat. No. 4,458,066.

In some embodiments, the 3'-end of the U-containing inhibitor oligonucleotide is blocked to prevent extension by the DNA polymerase. In some embodiments, a blocking group (a chemical moiety) is added to the terminal 3'-OH or 2'-OH in the oligonucleotide. Some non-limiting examples of blocking groups include an alkyl group, non-nucleotide linkers, phosphate group, phosphothioate group, alkane-diol moieties or amino group. In other examples, the 3'-hydroxyl group is modified by substitution with hydrogen for fluorine or by formation of an ester, amide, sulfate or glycoside. In yet another example, the 3'-OH group is replaced with hydrogen (to form a dideoxynucleotide).

In other embodiments, the invention is a method of modulating inhibition of the DNA polymerase by the dU-containing inhibitor oligonucleotide. The oligonucleotide of the present invention contains uracils. The presence of uracils in the DNA sequence makes the oligonucleotide a target for uracil DNA glycosylases. These enzymes recognize uracils present in single-stranded or double-stranded DNA and cleave the N-glycosidic bond between the uracil base and the deoxyribose, leaving an abasic site. See e.g. U.S. Pat. No. 6,713,294. Uracil-DNA glycosylases, abbreviated as "UDG" or "UNG" include UNG (EC 3.2.2.3), mitochondrial UNG1, nuclear UNG2, SMUG1 (single strand-selective uracil-DNA glycosylase), TDG (TU mismatch DNA glycosylase), MBD4 (uracil-DNA glycosylase with a methyl binding domain) and other eukaryotic and prokaryotic enzymes (See Krokan H. E. et al. (2002) *Uracil in DNA—occurrence, consequences and repair*, Oncogene 21:8935-9232).

Therefore according to the method of the invention, the reaction mixture no longer needs to be heated to the temperature exceeding the $T_m$ of the inhibitory oligonucleotide in order to unravel its secondary structure and release the inhibition of the enzyme in the oligonucleotide-enzyme complex. Instead, the reaction mixture containing the U-containing inhibitor oligonucleotide of the present invention is contacted by one of the uracil-N-glycosylases such as for example, UNG. Conveniently, UNG is active in a standard PCR reaction mixture. This enables adding UNG to assembled PCR reactions or even to the PCR master mix. Before the start of thermal cycling, the reaction mixture is incubated at a temperature optimal for the UNG activity within the context of the PCR master mix (about 50° C.) or within the temperature range where UNG is active. UNG will cleave off the uracil in the dU-containing inhibitor oligonucleotide leaving an abasic site. The backbone of DNA with abasic sites is known to be labile, especially at high temperature under high pH conditions. According to the invention, the one or more uracils and hence one or more abasic sites resulting from the UNG cleavage are located in the regions of the double stranded secondary structure, said structure will unravel upon cleavage and subsequent backbone cleavage.

In some embodiments, the method further comprises contacting the reaction mixture with a polyamine such for example, spermidine, spermine or trimethylenediamine as described in U.S. application Ser. No. 12/485,569 filed on Jun. 16, 2009. In some embodiments the polyamine is an intercalator amine. Polyamines of this group possess an intercalating moiety, capable of intercalating between the base pairs or bases in a nucleic acid. Examples of intercalating moieties on a polyamine include arenes and polyarenes, such as naphthalene and anthraquinone. In some embodiments, the intercalator moiety itself may also be substituted with one or more polyamine side chains. The addition of polyamines has been shown to facilitate degradation of abasic DNA resulting from UNG cleavage. Specifically at 50° C., the degradation is improved by 1000-fold.

According to the method of the invention, the U-containing inhibitor oligonucleotide can switch from stable secondary structure to unraveled structure at a lower temperature than oligonucleotide inhibitors described previously. This feature is especially beneficial for reaction mixtures and methods involving RNA templates that are labile in a typical reaction mixture under the temperature needed to release the enzyme inhibition. Release of the inhibition at lower temperatures will increase the efficiency of the reverse transcription step of RT-PCR by increasing the amount of available template.

In general, the U-containing inhibitor oligonucleotide of the present invention may be used in any method in which reversible inhibition of a DNA polymerase is desired. For example, the oligonucleotide can be used in DNA sequencing, DNA or RNA amplification, reverse transcription, reverse transcription PCR (RT-PCR), or primer extension, e.g., in detecting single nucleotide polymorphisms (SNPs) by single nucleotide primer extension.

In some embodiments, the invention is a method of amplification and optionally detection of a target nucleic acid sequence comprising contacting the sample in a reaction mixture (optionally a PCR reaction mixture containing all the components of PCR except the DNA polymerase) with a DNA polymerase and a reversible DNA-polymerase inhibitor in the form of a U-containing inhibitor oligonucleotide. In variations of this embodiment, the method further comprises contacting and incubating the reaction mixture with uracil-N-glycosylase enzyme. In variations of this embodiment, the method further comprises simultaneously of subsequently incubating the reaction mixture with a polyamine, optionally selected from spermidine, spermine or trimethylenediamine. The incubation may take place at 40-65° C., or any one of the 40, 45, 50, 55, 60 or 65° C. or any temperature in between, e.g., at 50° C. The method further comprises amplification and optionally detection of the target nucleic acid by PCR.

In yet another embodiment, the invention is a reaction mixture for amplifying a target nucleic acid containing a reversible inhibitor of a nucleic acid polymerase comprising the U-containing inhibitor oligonucleotide of the present invention which is a single-stranded DNA oligonucleotide having one or more regions of double-stranded secondary structure, wherein at least one of said regions comprises at least one uracil base. In variations of this embodiment, the reaction mixture further contains uracil-N-glycosylase, such as UNG. In other variations of this embodiment, the reaction mixture further contains a polyamine, optionally selected from spermidine, spermine or trimethylenediamine. In further variations of this embodiment, the kit further comprises reagents for PCR or RT-PCR including without limitation, nucleic acid precursors (dNTPs or NTPs), the polymerase enzyme, oligonucleotides (primers and optionally, probes) and buffers suitable to support the activity of the enzyme. In some embodiments, the target nucleic acid is RNA. In some embodiments, the polymerase is selected from DNA polymerases from *Thermotoga maritima*, *Thermus aquaticus*, *Thermus thermophilus*, *Thermus flavus*, *Thermus filiformis*, *Thermus* species Sps17, *Thermus* species Z05, *Thermus caldophilus*, *Bacillus caldotenax*, *Thermotoga neopolitana*, and *Thermosipho africanus*. In some embodiments, the polymerase is the DNA polymerase from *Thermus* species Z05 or *Thermus thermophilus*.

In yet another embodiment, the invention is a kit for amplifying a target nucleic acid containing a reversible inhibitor of a nucleic acid polymerase comprising the U-containing inhibitor oligonucleotide of the present invention which is a single-stranded DNA oligonucleotide having one or more regions of double-stranded secondary structure, wherein at least one of said regions comprises at least one uracil base. In variations of this embodiment, the kit further contains uracil-N-glycosylase, such as UNG. In further variations of this embodiment, the kit further contains a polyamine, optionally selected from spermidine, spermine or trimethylenediamine. In further variations of this embodiment, the kit further comprises reagents for PCR or RT-PCR including without limitation, nucleic acid precursors (dNTPs or NTPs), the polymerase enzyme, oligonucleotides (primers and optionally, probes) and buffers suitable to support the activity of the enzyme. In some embodiments, the polymerase is selected from DNA polymerases from *Thermotoga maritima*, *Thermus aquaticus*, *Thermus thermophilus*, *Thermus flavus*, *Thermus filiformis*, *Thermus* species Sps17, *Thermus* species Z05, *Thermus caldophilus*, *Bacillus caldotenax*, *Thermotoga neopolitana*, and *Thermosipho africanus*. In some embodiments, the polymerase is the DNA polymerase from *Thermus* species Z05 or *Thermus thermophilus*.

EXAMPLES

Example 1. Design of the U-Containing Inhibitor Oligonucleotides (U-Aptamers)

The existing aptamer NTQ21-46A (U0) (SEQ ID NO: 1) 5'-CGATCATCTCAGAACATTCTTAGCGTTTTGTTCT-TGTGTATGATCG-3' was modified by replacing dTs with dUs to create the following U-aptamers:

U1

(SEQ ID NO: 2)

5'-CGAUCAUCTCAGAACATTCTTAGCGTTTTGTTCTTGTGTAUGAUCG-3'

U2

(SEQ ID NO: 3)

5'-CGATCATCTCAGAACATTCTTAGCGTTTUGUUCUUGTGTATGATCG-3'

U3

(SEQ ID NO: 4)

5'-CGAUCAUCTCAGAACATTCTTAGCGTTTUGUUCUUGTGTAUGAUCG-3'.

The predicted secondary structure of the aptamers is shown on FIG. 1.

Example 2. Determination of the Melting Temperature of the U-Aptamers

Melting temperature of the U0, U1, U2 and U3 aptamers (SEQ ID NOs: 1, 2, 3 and 4) was determined in a reaction mixture containing 50 mm TrisHCl, pH 8.0, 100 mM KCl, 1 mM dNTPs, 2.5 mM MgCl$_2$, SYBR® Green I (Molecular Probes (Life Technologies, Inc.) Carlsbad, Calif.) at 0.5×, 20 nM DNA polymerase Z05-D (where indicated) and 0.2 µM of one of the aptamers. Melting curve analysis was performed in LightCyder® 480 (Roche Molecular Diagnostics, Indianapolis, Ind.) according to the manufacturer's instructions. The results are shown in Table 1. The results demonstrate that replacing Ts with Us lowers the melting temperature of the oligonucleotide secondary structure.

TABLE 1

Melting temperatures of aptamers

| Aptamer | dU content | $T_m$, °C. | |
|---|---|---|---|
| | | Z05D+ | Z05D− |
| U1 | Low | 58.4 | 56.8 |
| U2 | Medium | 59.5 | 57.9 |
| U3 | High | 57.6 | 55.6 |
| U0 | None | 60.7 | 59.0 |

Example 3. Determination of the Melting Temperature of the U-Aptamers in the Presence of UNG Melting temperature of the U0, U1, U2 and U3 aptamers (SEQ ID NOs: 1, 2, 3 and 4) was determined in a reaction mixture described in Example 1, except where indicated, 0.5 U/µL of UNG was added. To allow for UNG cleavage, all reaction mixtures were incubated at 37° C. prior to the melting curve analysis. The results are shown in Table 2. The results demonstrate that replacing Ts with Us and subsequent cleavage with UNG substantially lowers the melting temperature of the oligonucleotide secondary structure.

TABLE 2

Melting temperatures of aptamers after cleavage with UNG

| Aptamer | dU content | $T_m$, °C. | | | UNG $\Delta T_m$ |
|---|---|---|---|---|---|
| | | Z05D−/UNG− | Z05D−/UNG+ | Z05D+/UNG+ | |
| U1 | Low | 58.4 | 52.6 | 52.6 | 5.8 |
| U2 | Medium | 59.2 | 52.5 | 52.5 | 6.7 |
| U3 | High | 56.7 | 38.5 | 38.6 | 18.2 |
| U0 | None | 60.6 | 60.4 | 60.5 | 0.2 |

Example 4. Primer Extension in the Presence of U-aptamers and UNG at Different Temperatures The DNA polymerase activity in the presence of oligonucleotide inhibitors was determined by primer extension in the presence of various concentrations of the U0, U1, U2 or U3 aptamers (SEQ ID NOs: 1, 2, 3 and 4). The assay was performed using M13 mp18 single-stranded DNA (M13; GenBank Accession No. X02513), primed with an oligonucleotide having the following sequence (SEQ ID NO: 5):

5'-GCGCTAGGGCGCTGGCAAGTGTAGCGGTCAC-3'

Reactions were initiated by the addition of 12.5 µL of MgCl$_2$ to 12.5 µL of reaction master mix containing 1 nM of primed M13 template in 96-well PCR plates. Extension of the primed template was monitored every 6 seconds for 99 cycles on the LightCyder® 480 thermal cycler at the temperatures indicated. Master mixes contained 2.5 mM MgCl$_2$, 50 mM Tris pH 8.0, 100 mM KCl, a mixture of all four dNTPs, 20 nM of the Z05-D DNA polymerase and SYBR® Green I (Life Technologies, Carlsbad, Calif.) at 0.5×, which allowed for the fluorescent detection of primer strand extension. The concentration range of aptamers tested was 0, 50, 200, 2000 nM, to ensure that aptamers were present in a 0, 2.5, 10, or 100× molar excess relative to the Z05-D DNA polymerase (see figure legends on FIGS. 2-5). The DNA polymerase activity was quantified by determining the slope of increasing fluorescence over time in a linear range. The relative activities were calculated by normalizing to the average slope of all reactions conducted in the absence of aptamer at each temperature. The results are shown in FIGS. 2-5. The results demonstrate that the addition of UNG drastically reduces aptamer inhibition of the DNA polymerase, particularly for U3.

Example 5. Real Time PCR Amplification of KRAS Codon 12 target in the Presence of U-Aptamers and UNG In this example, amplification of the KRAS target in human DNA is performed in the presence of various concentrations of the U0, U1, U2 or U3 aptamers (SEQ ID NOs: 1, 2, 3 and 4). The nature of the KRAS target makes it especially vulnerable to primer dimerization and non-specific amplification. In the absence of hot start, the non-specific amplification obscures the differences in the target concentration and precludes quantitative analysis. In this example, serial ten-fold dilutions of the KRAS target were added to assess quantitative range and specificity of the method. Amplification was performed in a reaction mixture containing 3 mM MgCl$_2$, 50 mM Tricine pH 8.0, 55 mM potassium acetate, 200 µM each dATP, dCTP and dGTP, 300 µM dUTP, 30 µM dTTP, 20 nM of the Z05 DNA polymerase and SYBR® Green I (Life Technologies, Carlsbad, Calif.) at 0.2×, and UNG where indicated. The temperature profile in the LightCycler instrument was 50 cycles of 95° C. 15 sec, 50, 55 or 60° C. 40 seconds. Amplification was detected by measuring $C_t$ values in the presence of various concentrations of the U0, U1, U2 or U3 aptamers (SEQ ID NOs: 1, 2, 3 and 4). The concentration range of aptamers tested was 0, 200, 1000, and 2000 nM, to ensure that aptamers were present in a 0, 10, 100, or 200× molar excess relative to the Z05 DNA polymerase. The results are shown in Tables 3-6.

TABLE 3

Amplification of the KRAS target ($C_t$) without UNG, 60° C. 10x excess aptamer

| Target copy # | Aptamer | | | | |
|---|---|---|---|---|---|
| | none | U0 | U1 | U2 | U3 |
| $10^4$ | 24.5 | 25.1 | 25.1 | 25.0 | 25.0 |
| $10^3$ | 25.6 | 28.4 | 28.3 | 28.1 | 28.2 |
| $10^2$ | 25.8 | 31.1 | 30.8 | 30.6 | 30.3 |
| none | 25.7 | 32.0 | 31.7 | 31.2 | 30.8 |

TABLE 4

Amplification of the KRAS target ($C_t$) without UNG, 60° C. 100x, 200x excess aptamer

| Aptamer | Target Copy # | Aptamer 100x | Aptamer 200x | No Aptamer |
|---|---|---|---|---|
| U0 | $10^4$ | 32.8 | 33.1 | |
| | $10^3$ | 29.2 | 29.4 | |
| | $10^2$ | 25.7 | 26.0 | |
| | none | 37.7 | 38.7 | |
| U1 | $10^4$ | 32.6 | 32.7 | |
| | $10^3$ | 28.9 | 29.0 | |
| | $10^2$ | 25.6 | 25.7 | |
| | none | 37.2 | 38.3 | |
| U2 | $10^4$ | 32.4 | 32.5 | |
| | $10^3$ | 28.9 | 29.1 | |
| | $10^2$ | 25.7 | 25.6 | |
| | none | 36.6 | 38.0 | |
| U3 | $10^4$ | 32.0 | 31.6 | |
| | $10^3$ | 28.7 | 28.9 | |
| | $10^2$ | 25.4 | 25.6 | |
| | none | 36.4 | 37.3 | |
| none | $10^4$ | | | 26.3 |
| | $10^3$ | | | 26.1 |
| | $10^2$ | | | 24.7 |
| | none | | | 26.2 |

The results in Tables 3-4 demonstrate that the aptamers are required to determine concentration based on $C_t$ values and at 60° C. in the absence of UNG, the U-containing aptamers (SEQ ID NOs: 2, 3 and 4) behave similarly to the parent aptamer (SEQ ID NO: 1).

TABLE 5

Amplification of the KRAS target ($C_t$), 55° C.

| Aptamer | Target Copy # | UNG− | UNG+ |
|---|---|---|---|
| U0 | $10^2$ | 33.9 | 39.7 |
| | $10^3$ | 30.4 | 35.8 |
| | $10^4$ | 26.9 | 32.5 |
| | None | 39.9 | 43.3 |
| U1 | $10^2$ | 33.3 | 35.8 |
| | $10^3$ | 29.6 | 32.8 |
| | $10^4$ | 26.1 | 29.2 |
| | None | 39.9 | 38.7 |

TABLE 5-continued

Amplification of the KRAS target ($C_t$), 55° C.

| Aptamer | Target Copy # | UNG− | UNG+ |
|---|---|---|---|
| U2 | $10^2$ | 33.4 | 35.5 |
| | $10^3$ | 29.8 | 32.5 |
| | $10^4$ | 26.3 | 28.8 |
| | None | 39.5 | 38.0 |
| U3 | $10^2$ | 32.6 | 34.8 |
| | $10^3$ | 29.1 | 31.8 |
| | $10^4$ | 25.7 | 28.1 |
| | None | 37.6 | 36.0 |
| None | $10^2$ | 25.9 | 27.6 |
| | $10^3$ | 25.8 | 27.3 |
| | $10^4$ | 24.6 | 27.0 |
| | None | 25.9 | 27.4 |

TABLE 6

Amplification of the KRAS target ($C_t$), 50° C. 200x excess aptamer

| Aptamer | Target Copy # | UNG− | UNG+ |
|---|---|---|---|
| U0 | $10^2$ | 35.3 | 0.0 |
| | $10^3$ | 31.6 | 36.9 |
| | $10^4$ | 28.0 | 33.7 |
| | None | 44.3 | 41.2 |
| U1 | $10^2$ | 34.9 | 35.8 |
| | $10^3$ | 30.8 | 32.4 |
| | $10^4$ | 27.4 | 28.8 |
| | None | 44.7 | 44.4 |
| U2 | $10^2$ | 34.6 | 35.2 |
| | $10^3$ | 30.9 | 31.9 |
| | $10^4$ | 27.6 | 28.0 |
| | None | 41.3 | 39.1 |
| U3 | $10^2$ | 33.9 | 34.0 |
| | $10^3$ | 30.3 | 30.5 |
| | $10^4$ | 26.7 | 26.9 |
| | None | 40.2 | 38.7 |
| None | $10^2$ | 26.9 | 28.7 |
| | $10^3$ | 26.6 | 28.6 |
| | $10^4$ | 25.0 | 27.5 |
| | None | 26.9 | 28.8 |

The results in Tables 5-6 demonstrate that at lower annealing temperatures and increased aptamer concentrations, the addition of UNG drastically reduces dU-containing aptamer inhibition of the DNA polymerase, particularly for U3, as demonstrated by lower $C_t$ values.

Example 6. RT PCR Amplification of RNA in the Presence of U-Aptamers and UNG

In this example, amplification of an RNA target (HCV JP2-5, 1000 copies per reaction) was performed in the presence of various concentrations of the U0, U1, U2 or U3 aptamers (SEQ ID NOs: 1, 2, 3 and 4) in the reaction mixture containing UNG as described in Example 5 under the standard PCR conditions. The concentration range of aptamers tested was none, 100-fold and 200-fold molar excess relative to the Z05 DNA polymerase. The results are shown in Table 7.

TABLE 7

Amplification of the HCV RNA target ($C_t$) at 55° C.

| Aptamer | Fold excess of aptamer to enzyme | $C_t$ |
|---|---|---|
| U0 | 10 | ND |
| | | ND |

TABLE 7-continued

Amplification of the HCV RNA target ($C_t$) at 55° C.

| Aptamer | Fold excess of aptamer to enzyme | $C_t$ |
|---|---|---|
|  | 100 | ND |
|  |  | ND |
|  | 200 | ND |
|  |  | ND |
| U1 | 10 | 33.5 |
|  |  | 33.7 |
|  | 100 | ND |
|  |  | ND |
|  | 200 | ND |
|  |  | ND |
| U2 | 10 | 32.8 |
|  |  | 32.48 |
|  | 100 | 32.8 |
|  |  | 32.57 |
|  | 200 | 35.66 |
|  |  | 35.85 |
| U3 | 10 | 32.62 |
|  |  | 32.57 |
|  | 100 | 32.48 |
|  |  | 32.16 |
|  | 200 | 33.32 |
|  |  | 33.13 |

ND = not detected

The results in Table 7 demonstrate that at lower annealing temperatures (e.g., 55° C.) the dU-containing aptamers in the presence of UNG have reduced inhibition of the DNA polymerase, as demonstrated by lower $C_t$ values.

While the invention has been described in detail with reference to specific examples, it will be apparent to one skilled in the art that various modifications can be made within the scope of this invention. Thus the scope of the invention should not be limited by the examples described herein, but by the claims presented below.

What is claimed:

1. A method of reversibly inhibiting a nucleic acid polymerase in a reaction mixture comprising contacting the mixture with a single-stranded DNA oligonucleotide having more than one regions of double-stranded secondary structure and comprising SEQ ID NO: 1, wherein more than one thymine bases are replaced with uracil bases only in at least one of the more than one regions of double-stranded secondary structure, and wherein the more than one regions of double-stranded secondary structure are stable under ambient temperature in a PCR mixture.

2. The method of claim 1, further comprising contacting the reaction mixture with a uracil-N-glycosylase.

3. The method of claim 2, wherein the contacting takes place in the temperature range of 40-65° C.

4. The method of claim 1, further comprising contacting the reaction mixture with a polyamine.

5. The method of claim 4, wherein the polyamine is selected from spermidine, spermine and trimethylenediamine.

6. A method of amplifying a target nucleic acid comprising prior to amplification, contacting a reaction mixture containing the target nucleic acid with a single-stranded DNA oligonucleotide having more than one regions of double-stranded secondary structure and comprising SEQ ID NO: 1, wherein more than one thymine bases are replaced with uracil bases only in at least one of the more than one regions of double-stranded secondary structure, and wherein the more than one regions of double-stranded secondary structure are stable under ambient temperature in a PCR mixture.

7. The method of claim 6, further comprising prior to amplification, contacting the reaction mixture with a uracil-N-glycosylase.

8. The method of claim 6, further comprising contacting the reaction mixture with a polyamine.

9. The method of claim 8, wherein the polyamine is selected from spermidine, spermine and trimethylenediamine.

10. The method of claim 1, wherein the single-stranded DNA oligonucleotide comprises a nucleotide sequence selected from SEQ ID NO: 2, 3, or 4.

11. The method of claim 6, wherein the single-stranded DNA oligonucleotide comprises a nucleotide sequence selected from SEQ ID NO: 2, 3, or 4.

* * * * *